United States Patent [19]

de Kreuk

[11] 4,220,515

[45] Sep. 2, 1980

[54] APPARATUS FOR AUTOMATICALLY DETERMINING THE AMOUNT OF ONE OR MORE SUBSTANCES IN A LIQUID

[75] Inventor: Casper W. de Kreuk, Bleiswijk, Netherlands

[73] Assignee: Nederlandse Organisatie voor Toegepast-Natuurwetenschappelijk Onderzoek ten behoeve van Nijverheid, Handel en Verkeer, The Hague, Netherlands

[21] Appl. No.: 964,106

[22] Filed: Nov. 27, 1978

[30] Foreign Application Priority Data

Jan. 10, 1978 [NL] Netherlands ............................ 7800279

[51] Int. Cl.³ ............................................ G01N 27/34
[52] U.S. Cl. ................................................ 204/195 H
[58] Field of Search ......................... 204/195 H, 1 T

[56] References Cited

U.S. PATENT DOCUMENTS

| 3,922,205 | 11/1975 | McLean et al. | 204/1 T |
| 4,138,322 | 2/1979 | Barnes et al. | 204/195 H |

FOREIGN PATENT DOCUMENTS 172112  6/1965  U.S.S.R. ............................ 204/195 H

OTHER PUBLICATIONS

M. D. Booth et al., Talanta, 17, 1059-1065, (1970).

Primary Examiner—G. L. Kaplan
Attorney, Agent, or Firm—Ladas & Parry

[57] ABSTRACT

A method for automatically determining the amount of one or more substances by stripping voltammetry, said amount ranging from $10^{-9}$ to $10^{-5}$ mol/l (0.1–1000 microgrammes per liter) according to an automatically repeating programme is carried out continuously, not batch-wise, for a time span of a month or more. An apparatus implementing said method preferably comprises a hanging drop electrode and means to renew the hanging drop at the start of each determination. Pretreatment of a physical and/or chemical nature is carried through continuously outside the stripping range. (FIG. 1).

3 Claims, 3 Drawing Figures

APPARATUS FOR AUTOMATICALLY DETERMINING THE AMOUNT OF ONE OR MORE SUBSTANCES IN A LIQUID

The invention relates to a method for automatically determining the amount of one or more substances in a liquid in a measuring cell comprising an electrode system with a mercury electrode by stripping voltammetry, said amount being of the order of magnitude of $10^{-9}$ to $10^{-5}$ mol/l (0,1–1000 micrograms/l) wherein the liquid preceding said determination is subjected to chemical and physical treatments to bring about the correct conditions for the voltammetric determination and a programme is pursued which automatically repeats itself. The invention relates, moreover, to an apparatus for implementing said method.

A similar method and apparatus are known from an article by M. D. Booth, M. J. D. Brand and B. Fleet in Talanta 17 (1970), 1059–1065. According to the known method the programme consists in introducing a sample of the liquid into the measuring cell together with auxiliary substances for a chemical treatment of the liquid such as for enabling adjusting the degree of acidity, and for a physical treatment, for example nitrogen to eliminate oxygen being dissolved in the liquid therefrom, then enabling the reaction of these auxiliary substances in the measuring cell, thereafter carrying out the voltammetric determination in the treated liquid in the measuring cell and finally rinsing and measuring cell clean. The determination is carried out using a rotating mercury-coated platinum electrode.

When one is faced with the problem of applying the method of the type described in the preamble in determining the amount of metals in surface water, for example, which determination in view of the preparation of drinking water from available surface water must take place continuously over a long period of time, preferably in an unguarded automatic measuring station, the operation of the apparatus implementing said method must be as reliable as possible. The known method proceeding as an essentially discontinuous process required measures which bring about the closing and opening of transport lines according to the cyclically repeated programme for feeding the liquid sample and the auxiliary substances in a first phase and discharging the prepared sample after completion of the determination in a following phase and finally for rinsing the measuring cell. All these measures are just as many sources of failure when the apparatus is used for such a long time as is envisaged. Further, according to the known method, the mercury-coated platinum electrode becomes fouled more quickly in the envisaged circumstances, so that measurement results obtained in the course of a few days are not comparable. In other words, the life time of the mercury electrode in the known method limits the possibility of leaving the apparatus unguarded, certainly if from a few dozen to a hundred determinations a day have to be carried out in the same measuring cell.

According to the invention a very reliable method of the type described in the preamble is characterized by allowing the liquid in which the determination must be carried out to flow continuously through spaces in which the chemical and physical pre-treatments take place and, at least for the time available in the programme for depositing the substances from the liquid into the mercury electrode, through the measuring cell, and by the whole renewal of the mercury electrode at the beginning of the programme, the liquid being mechanically stirred in the measuring cell during the deposition.

An advantage of the method of the invention is that the carrying out of the chemical and physical treatments in the feeding system to bring about the correct conditions for the voltammetric determination enables the carrying out of these treatments without considering the properties of the measuring cell, which properties might be affected by said treatments. For example, the liquid can be heated with a view to releasing the ions to be determined.

The apparatus implementing the method of the invention and comprising a measuring cell, a system feeding the liquid to be tested and the auxiliary substances for chemical and physical pre-treatments, a mercury electrode contained in the measuring cell, a discharge system for the liquid and the auxiliary substances and a programming circuit for the automatic carrying out of the measurement is characterized in that the mercury electrode is a hanging drop electrode and in that the supply system contains spaces for carrying out the physical and chemical treatments and a means for supplying mercury to the electrode in doses, the measuring cell being provided with a knocking device and a magnetic stirring member, the control of which knocking device and stirring member is incorporated in the programming circuit.

The invention is now to be illustrated in a description of a preferred embodiment, which description refers to a drawing.

FIG. 1 in the drawing is a diagram of the implementation of a measuring cell with accessories.

Figure 1:
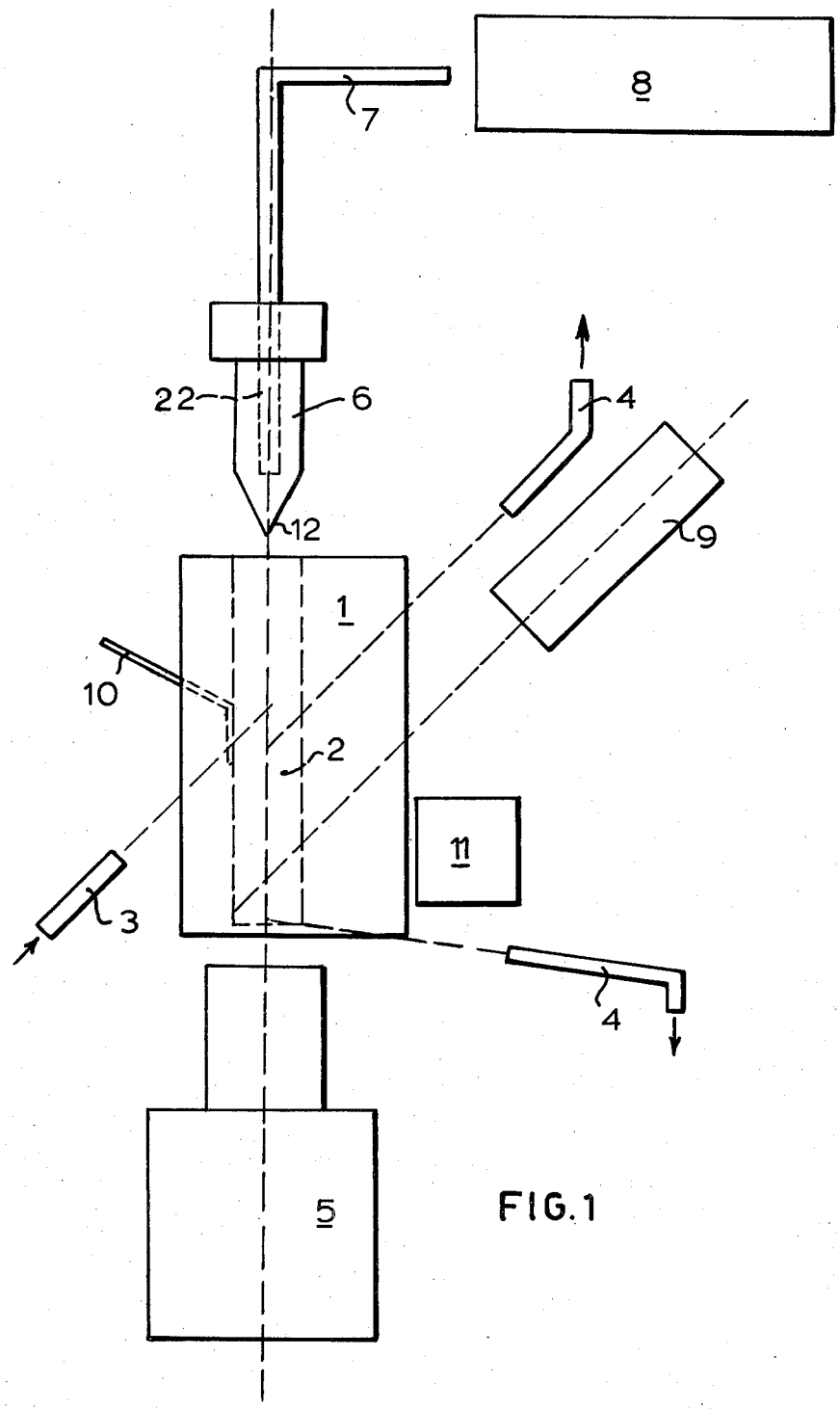

In FIG. 1 the measuring cell whose liquid volume is less than 1 cm$^3$ is represented in an exploded view on a scale of 2 to 1 approximately.

In the block-shaped housing 1 of the measuring cell a cavity 2 has been arranged which can be shut off by a plug 6 which is also the member from which the mercury drop forming the measuring electrode can hang. For this purpose, the plug 6 is provided with a pointed extremity 12 which is hollow. The bore (not shown) in the pointed extremity 12 is connected with a bore 22 in the plug 6, which bore is connected through a line 7 to a device 8 for the exact dosage of mercury from a reservoir (not shown).

In the housing 1 openings (not shown) which are connected to cavity 2 have been arranged for inserting a feeding line 3 and a system of discharge lines 4 respectively. Further, an opening (not shown) has been arranged in the housing for inserting a reference electrode 9 such as a silver-silver chloride electrode and an opening for inserting a counter electrode 10.

Beneath the closed bottom end of cavity 2 there is a drive 5 for a magnetic stirring member which fits into cavity 2. A knocking device 11 has been arranged adjacent to one of the side walls of the housing 1 which knocking device 11, activated by a control signal, imparts a movement to the housing such that a mercury drop hanging from the pointed tip end 12 of the plug 6 is released and falls through cavity 2, whereupon the drop can be washed away with the tested liquid through discharge line 4.

The said parts of the measuring cell can be advantageously manufactured from an optionally transparent plastic material. This is particularly true of the plug 6, at least for the pointed tip end 12 thereof, now it seems that the reproducibility, purity and suspension of the mercury drop are favourably influenced by an implementation of the plug in a plastic material compared with an implementation in glass. The hydrophilic characteristics of glass are detrimental to the reproducibility of the mercury drop. The mercury drop has a surface area in the order of magnitude of 1 mm$^2$.

Figure 2:
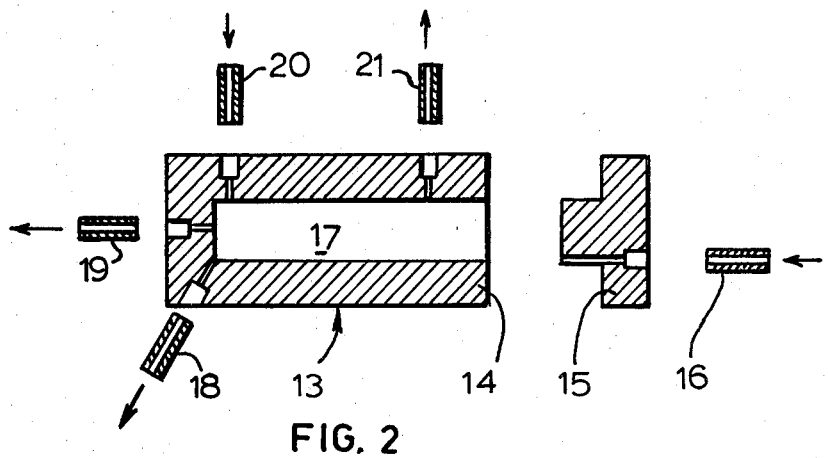
FIG. 2 is a diagram of a cell for eliminating oxygen from the liquid to be tested.

The feeding system comprises a cell in which the elimination of oxygen from the liquid occurs according to the counterflow principle, whilst the liquid flows in a film along a wall of the cell. In FIG. 2 such a cell 13 is drawn in its approximate true size. The housing of the cell 13 is composed of two parts 14 and 15, which parts determine a cylindrical cavity 17. Access is given to the cavity 17 by an opening in part 15 for a connecting tube 16 and openings in part 14 for, respectively, a connecting tube 18, a connecting tube 19, a connecting tube 20 and a connecting tube 21. While orienting the axis of the cylindrical cavity 17 at an angle of about 30° with the horizon in such a way that the connecting tube 21 is connected to the highest point of cavity 17, the cell 13 operates as follows. The liquid to be treated, preferably segmented with nitrogen bubbles, is introduced into the cell cavity 17 via the connecting tube 16. The liquid can leave the cell cavity 17 via the connecting tube 18. Nitrogen enters the cell cavity 17 through the connecting tube 20 and the connecting tube 21 enables the introduced nitrogen to leave the cell cavity 17 including the oxygen liberated from the liquid. The liquid supply to and its discharge from the cell are adjusted in such a way that rather more liquid enters the cell than can leave the cell by the connecting tube 18 in the direction of the measuring cell. The surplus liquid is discharged to the draining system via the connecting tube 19 serving as an overflow. The segmenting bubbles and the counterflow of nitrogen in the cell cavity 17 cause the liquid to leave the cell cavity substantially free of oxygen.

Figure 3:
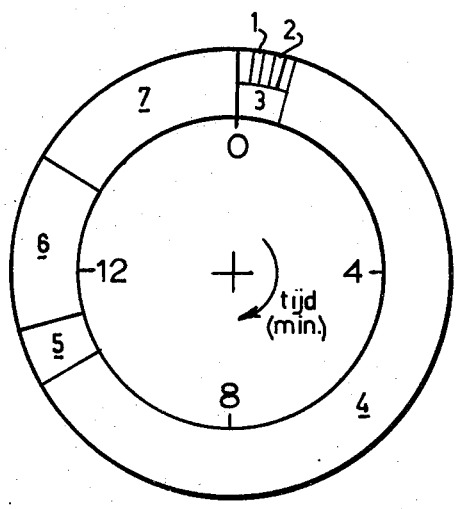
FIG. 3 represents one cycle of the programme.

The programme which is followed in determining metals in water is diagrammatically represented in FIG. 3. The liquid wherein the amount of, among others, zinc, copper, lead and cadmium must be determined, flows continuously through the feeding system and the drainage system. The programme begins with the knocking off of the mercury drop used during the preceding programme as a hanging electrode. The drop disappears in the liquid flow through the drainage system (phase 1). Subsequently, a fresh mercury drop is formed (phase 2). For a certain period of time (less than 30 seconds) the potential of the mercury electrode is kept just above that of the reference electrode (phase 3). This potential difference is for example +150 mV with respect to the silver-silver chloride reference electrode. Subsequently, by applying a sufficiently high potential difference between mercury electrode and reference electrode, for example −1225 mV for about 10 minutes, the deposition of the sought metals from the treated liquid onto the mercury drop is aimed at whilst continuously stirring the liquid adjacent to the mercury drop mechanically, so that the liquid directly around the drop is continuously replaced. After the time period allowed for the deposition the programme introduces a short pause (20 seconds) in which the mercury electrode is kept at a potential which does not have to be the same as the deposition potential and in which the stirring is stopped (phase 5). After the pause, the potential difference is brought gradually according to the programme and as, for example, a linear function of time to +150 mV, the metal atoms deposited in the mercury electrode again being ionized and dissolved (phase 6). The amounts of the substances thus being stripped (metals in the example discussed here) are calculated from the electric current measured during this period of time. By then carrying out a similar potential programme and a measurement of the electric current the background or datum line for the electric current measured during the redissolution or stripping is obtained (phase 7).

Instead of realizing a potential of the mercury drop electrode that is linearly increasing with time, the potential programme intended for the redissolution can be implemented for a differential pulse-analysis with a view to enhancing the sensitivity of the determination.

In order to realize the determination of the amount of metal ions against a normalized background according to a variant of the above method the redissolution of the deposited substances from the mercury electrode takes place following the deposition in a flow of a standard liquid, the treated liquid being led round the measuring cell during the redissolution.

The method of the invention and the apparatus implementing the method are of such appropriateness that the programme can be continuously repeated for at least a month. Consequently, the device is excellently suited for an unguarded automatic measuring station and is then controlled by a programmed processor constituting the programming circuit. The results of the measurement can be transmitted to a central station by telemetry, apart or integrated.

It is pointed out that by the pretreatment in the feeding system of the liquid wherein the determination must be carried out, these treatments cannot influence the properties of the actual measuring cell. For example, heating to a temperature of 90° C. and adding a strong acid can be used for releasing the metal ions. This is of particular importance in examining the polluted surface water such as is found in large rivers.

What is claimed is:

1. Apparatus for automatically determining the amount of one or more substances in a liquid by stripping voltammetry, comprising:
   a measuring cell;
   electrode support means disposed in the measuring cell for supporting a drop of mercury therein as a hanging drop electrode;
   a feeding system for delivering liquid to the measuring cell for testing and for delivering mercury in doses to the electrode support means, said feeding system including a pretreatment chamber in which liquid undergoes pretreatment prior to being delivered to the measuring cell for testing;
   a discharge system for removing the liquid from the measuring cell after testing;
   a magnetic stirring device for stirring the liquid in the measuring cell;
   a knocking device for knocking the measuring cell thereby to detach the mercury drop from the electrode support means, the deteached mercury drop leaving the cell with the liquid by way of the discharge system; and
   a programming circuit for automatically controlling operation of the apparatus, said programming circuit being connected to control operation of the stirring device and the knocking device.

2. Apparatus as claimed in claim 1, wherein the feeding system includes a pretreatment chamber in which liquid undergoes pretreatment for elimination of oxygen from the liquid, said pretreatment chamber being bounded by a cylindrical wall and two opposite end faces, and being provided with a feeder opening and a discharge opening for nitrogen arranged along a generatrix of the cylindrical wall near the end faces respectively of the chamber, a feeder opening and a discharge opening for the liquid to be pretreated arranged substantially diametrically opposite to the openings for nitrogen, and an overflow opening for liquid in one end face, so that by placing the chamber with the central axis of the cylindrical wall inclined to the horizontal a film of liquid is able to flow from the feeder opening for liquid to the discharge opening for liquid and to the overflow in counterflow to a nitrogen stream.

3. Apparatus as claimed in claim 1 or 2, wherein the electrode support means are formed from plastics material.

* * * * *